United States Patent [19]

Descamps et al.

[11] 4,330,542

[45] May 18, 1982

[54] N(SULFONYL)ANILINES FOR TREATING ANGINA PECTORIS

[75] Inventors: Marcel Descamps, Rosieres; Charles Goldenberg, Brussels, both of Belgium

[73] Assignee: Sanofi, Paris, France

[21] Appl. No.: 150,411

[22] Filed: May 16, 1980

[30] Foreign Application Priority Data

Jun. 14, 1979 [FR] France ................. 79 15232

[51] Int. Cl.³ ............... A61K 31/535; A61K 31/495; C07D 295/08
[52] U.S. Cl. ................. 424/248.5; 544/165; 544/398; 544/401; 564/86; 564/89; 564/90; 564/93; 424/250; 424/274; 424/321; 548/561; 548/569
[58] Field of Search .............. 544/394, 401, 165; 564/89, 86, 90–93; 424/250, 248.5, 274, 321; 260/326.58 F

[56] References Cited

U.S. PATENT DOCUMENTS 2,575,122 11/1951 Pollard et al. ............. 544/394
3,917,598 11/1975 Maruyama et al. ......... 544/394
4,112,231 9/1978 Weibull et al. ............. 544/401

FOREIGN PATENT DOCUMENTS 22118 1/1981 European Pat. Off. .

Primary Examiner—Anton H. Sutto
Attorney, Agent, or Firm—Mason, Kolehmainen, Rathburn & Wyss

[57] ABSTRACT

The invention relates to novel aniline derivatives of the formula:

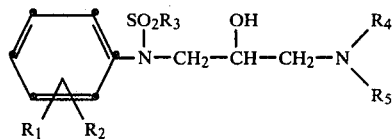

wherein $R_1$ and $R_2$ represent a hydrogen or chlorine atom, an allyloxy, acetamide or carboxamide group, $R_3$ represents a methyl or an optionally substituted phenyl group, $R_4$ represents a hydrogen atom and $R_5$ an isopropyl, terbutyl, 2-phenoxy-ethyl or 3-phenyl-propyl group or $R_3$ and $R_5$ taken together form with the nitrogen atom a substituted heterocyclic group.

The compounds of the invention are useful for the treatment of angina pectoris.

22 Claims, No Drawings

N(SULFONYL)ANILINES FOR TREATING ANGINA PECTORIS

This invention relates to novel aniline derivatives and to pharmaceutical compositions containing the same. The invention also relates to a process for preparing these aniline derivatives and to a method of treatment of angina pectoris.

The aniline derivatives with which the invention is concerned are the compounds of the general formula:

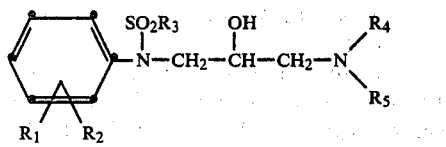

and the pharmaceutically acceptable acid addition salts thereof, wherein $R_1$ and $R_2$, which are the same or different, represent an allyloxy, acetamide or carboxamide group, or a hydrogen or chlorine atom, $R_3$ represents a methyl, phenyl, methylphenyl or methoxyphenyl group, $R_4$ represents a hydrogen atom and $R_5$ an isopropyl, terbutyl, 2-phenoxyethyl, 3-phenylpropyl group or $R_4$ and $R_5$ taken together form with the nitrogen atom a heterocycle such as pyrrole, morpholine, a substituted piperazine of the formula:

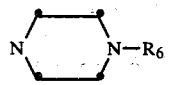

wherein $R_6$ represents a straight-chain alkyl group containing from 1 to 3 carbon atoms, a 2-hydroxyethyl, a benzyl or a 2-pyridyl group or a phenyl group optionally substituted by either a halogen atom or by a methoxy radical.

The compounds of formula I can be prepared by reacting an amine of the general formula:

wherein $R_4$ and $R_5$ have the same meanings as hereabove, with a compound of the general formula:

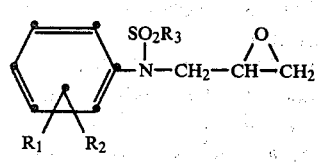

wherein $R_1$, $R_2$ and $R_3$ have the same meanings as hereabove. This reaction is carried out in an alcoholic solvent such as, for example, ethanol.

The amines of formula III are compounds which are readily available on the market.

The epoxides of formula IV are prepared by condensing a sulphonamide of the general formula:

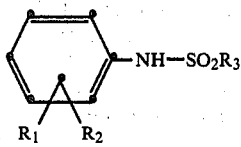

wherein $R_1$, $R_2$ and $R_3$ have the same meanings as hereabove, with an epihalohydrine such as, for example, epichlorhydrine.

The sulphonamides of formula V are prepared by condensing a substituted aniline of the formula:

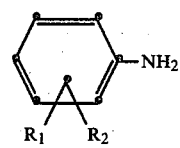

wherein $R_1$ and $R_2$ have the same meanings as hereabove, with a sulphonyl chloride of the formula:

wherein $R_3$ has the same meanings as hereabove.

The anilines of formula VI are either commercially available or have been described by G. D. Tiffany in J. Am. Chem. Soc., 1948, 70, 592 and by J. Degutis and D. Sukeliene in Zh. Obshch. Khim. 1961, 31, 3326. The sulphonyl chlorides of formula VII are available on the market. The compounds of the invention have been found to possess useful pharmacological properties likely to render them of particular value in the treatment of pathological conditions of the heart.

More particularly, they have been found to possess very useful properties for the treatment of angina pectoris.

Another object of the invention is therefore a method of treatment of pathological conditions of the heart, in particular angina pectoris, consisting in administering to a patient in need of such treatment at least one compound of formula I or one of its non-toxic acid addition salts.

It is well known that pathological conditions of the heart are very difficult diseases to master.

This is particularly true in the case of angina pectoris, since there are many factors which may provoke an attack of angor.

The considerable number of factors thus involved justifies the presentday approach to the therapeutic treatment of angina pectoris. According to modern thinking, the medicinal value of an active principle is in direct proportion to the polyvalent nature of its pharmacological activity.

It has been found that the compounds of the invention provoke bradycardia and diminish arterial pressure, properties which are useful for obtaining a better energetic performance of the myocardium. It has also been found that the compounds of the invention possess valuable antiadrenergic properties, not only with respect to the $\alpha$ system but also to the $\beta$ system.

These properties enable the heart to be protected against the hypermetabolic action of the catecholamines and, as a result also contribute to improving cardiac performance.

The pharmacological investigation was carried out on anaesthetized dogs (30 mg/kg I.V. of sodium pentobarbital) having previously received an intravenous dose of 1 mg/kg of atropine sulphate.

The substance to be tested was given by an intravenous injection lasting two minutes after which the behaviour of both heart-rate and blood-pressure was observed over a certain period of time. An investigation was then carried out to detect any antiadrenergic properties. The compound listed hereunder were tested, in most cases in the form of pharmaceutically acceptable acid addition salts:

| Compounds | N° code |
|---|---|
| 2-Allyloxy-N-(3-tert-butylamino-2 hydroxy-propyl)-N-(4-methoxy-benzenesulphonyl)-aniline | 14 |
| 2-Allyloxy-N-[3-(4-(4-fluoro-phenyl)-1-piperazinyl)-2-hydroxy-propyl]-N-methylsulphonyl-aniline | 23 |
| 2-Allyloxy-N-[2-hydroxy-3-(4-(2-methoxy-phenyl)-1-piperazinyl)-propyl]-N-methylsulphonyl-aniline | 30 |
| 2-Allyloxy-N-[3-(4-benzyl-1-piperazinyl)-2-hydroxy-propyl]-N-(4-methylbenzene-sulphonyl)-aniline | 40 |
| 2-Allyloxy-N-[2-hydroxy-3-(4-(2-pyridyl)-1-piperazinyl)-propyl]-N-(4-methoxy-benzenesulphonyl)-aniline | 53 |
| 2-Allyloxy-N-[2-hydroxy-3-(4-(2-fluoro-phenyl)-1-piperazinyl)-propyl]-N-(4-methoxy-benzenesulphonyl)-aniline | 57 |
| 3,4-Dichloro-N-[3-(4-(2-chloro-phenyl)-1-piperazinyl)-2-hydroxy-propyl]-N-methylsulphonyl-aniline | 75 |
| 3,4-Dichloro-N-[2-hydroxy-3-(4-(2-methoxy-phenyl)-1-piperazinyl)-propyl]-N-methylsulphonyl-aniline | 77 |
| 3,4-Dichloro-N-[3-(4-(4-chloro-phenyl)-1-piperazinyl)-2-hydroxy-propyl]-N-(4-methoxy-benzenesulphonyl)-aniline | 84 |
| 4-Acetylamino-N-[2-hydroxy-3-(4-phenyl-1-piperazinyl)-propyl]-N-methylsulphonyl-aniline | 88 |
| 4-Acetylamino-N-[2-hydroxy-3-(4-(2-methoxy-phenyl)1-piperazinyl)-2-hydroxy-propyl]-N-methyl-sulphonyl-aniline | 90 |
| 4-Acetylamino-N-[2-hydroxy-3-(4-phenyl-1-piperazinyl)-propyl]-N-(4-methyl-benzenesulphonyl)-aniline | 91 |
| 4-Acetylamino-N-[2-hydroxy-3-(4-(2-methoxy-phenyl)-1-piperazinyl)-propyl]-N-(4-methyl-benzenesulphonyl)-aniline | 94 |
| 4-Acetylamino-N-[3-(4-(2-chloro-phenyl)-1-piperazinyl)-2-hydroxy-propyl]-N-(4-methyl-benzenesulphonyl)-aniline | 95 |
| N-[3-(4-(4-chlorophenyl)-1-piperazinyl)-2-hydroxy-propyl]-N-methylsulphonyl-4-amino-phenylacetamide | 99 |
| N-[2-hydroxy-3-(4-(2-methoxy-phenyl)-1-piperazinyl)-propyl]-N-methylsulphonyl-4-amino-phenylacetamide | 102 |
| N-[2-hydroxy-3-(4-(2-methoxy-phenyl)-1-piperazino)-propyl]-N-(4-methyl-benzenesulphonyl)-4-amino-phenylacetamide | 105 |

The following observations were made:

(1) Heart-rate

At a dose of 10 mg/kg, Compounds Nos. 14, 40, 57, 77, 84, 91, 94 and 102 provoked a marked and long-lasting reduction in heart-rate.

(2) Blood-pressure

At a dose of 10 mg/kg, Compounds Nos. 23, 30, 40, 53, 75, 77, 88, 90, 91, 94, 95, 102 and 105 caused a marked and constant reduction in blood-pressure.

(3) Antiadrenergic properties

The inhibitory effect of the compounds of the invention on the α-system was first determined by measuring the degree to which the said compounds reduced epinephrine-increased blood-pressure in the atropinized dog.

A dose of epinephrine, sufficient to produce a stable increase in blood-pressure was administered to a dog anaesthetized with sodium pentobarbital which had previously received an intravenous injection of 1 mg/kg of atropine sulphate. The operation was repeated several times and the blood-pressure obtained was noted. When the latter had returned to its normal level, the animal was given an intravenous dose of 10 mg/kg of the compound to be tested followed by the same dose as above of epinephrine.

Blood-pressure was recorded throughout the trial and it was observed that Compounds Nos. 14, 23, 30, 40, 53, 57, 75, 77, 84, 88, 90, 91, 94, 99, 102 and 105 reduced, at least partially, the epinephrine-induced arterial hypertension.

Long-lasting and total reduction was obtained with a dose as low as 2 mg/kg, for instance with Compounds Nos. 30 and 102.

The antiadrenergic effects of the compounds of the invention on the β-system were also studied, by determining the degree to which they reduced isoprenaline-increased heart-rate. The same method as above was used.

Compounds Nos. 14, 30, 40 and 88 produced a marked reduction in the isoprenaline-increased heart-rate, thus showing considerable β-antiadrenergic properties.

It is well known that the efficacy of an antianginal drug is at its maximum when the α antiadrenergic action is coupled with a β-antiadrenergic action and when the drug also causes a reduction in blood-pressure and heart-rate.

The compounds cited hereabove possess these properties and are therefore the preferred compounds of the invention.

Acute toxicity tests were also carried out on the rat, by intravenous route.

The $LD_{50}$ of Compound No. 40, i.e. the dose which kills half of the animals treated, was found to be 12 mg/kg.

For therapeutic use in the treatment of angor, 100 to 200 mg of the compounds of the invention will be administered daily in the form of a pharmaceutical composition containing an active principle at least one compound of formula I, or a pharmaceutically acceptable addition salt thereof together with a suitable excipient or carrier therefor.

The compounds of the invention will normally be adminstered in the form of a pharmaceutical composition appropriate to the desired mode of administration. Thus, the pharmaceutical composition may take the form of, for example, a coated or uncoated tablet or of a hard- or soft-gelatine capsule for oral administration or of a solution for injection or of a suppository for rectal administration.

Irrespective of the form which the pharmaceutical composition takes, the latter will normally comprise at least one of the compounds of formula I or a pharmaceutically acceptable acid addition salt thereof in association with an appropriate pharmaceutical excipient or carrier comprising, for example, one or more of the following substances: milk, sugar, starches, talc, magnesium stearate, polyvinylpyrrolidone, alginic acid, colloidal silica or a flavouring agent.

The following Example illustrates, in a non-limitative manner, the process for preparing the compounds of the invention.

PREPARATION OF 2-ALLYLOXY-N-(2-HYDROXY-3-ISO-PROPYLAMINO-PROPYL)-N-METHYLSULPHONYL-ANILINE.

(a) 2-Allyloxy-N-methylsulphonyl aniline

In a two-liter three-necked flask, fitted with a mechanical stirrer, a dropping-funnel and an air-inlet, were dissolved 149.2 g (1 mol) of 2-allyloxy-aniline in a mixture of 500 ml of benzene and 190 ml of pyridine.

A solution of 114.5 g (1 mol) of methane-sulphonyl-chloride in 195 ml of dimethylformamide and 70 ml of benzene was added drop-by-drop at room temperature.

The reaction medium was stirred at room-temperature for 24 hours and was poured into water.

Stirring was continued for one hour and the insoluble matter was filtered out.

The organic phase was decanted and the excess of pyridine was eliminated by washing with 20% hydrochloric acid.

The organic phase was then washed twice with water and then dried on anhydrous calcium sulphate.

The solvent was evaporated off under reduced pressure and the residue was recrystallized from isopropanol to give 178 g of 2-allyloxy-N-methylsulphonyl-aniline.

Yield: 78.3%. Melting Point: 90° C.

By following the same procedure as that described above but using the appropriate starting-products, the following compounds were prepared:

| Compounds | Melting Point °C. |
|---|---|
| 2-Allyloxy-N-(4-methyl-benzenesulphonyl)-aniline | 102 (isopropanol) |
| 2-Allyloxy-N-(4-methoxy-benzenesulphonyl)-aniline | 98 (isopropanol) |
| 2,6-Dichloro-N-benzenesulphonyl-aniline | 156 (ether) |
| 2,6-Dichloro-N-(4-methyl-benzenesulphonyl)-aniline | 158 (isopropanol) |
| 3,4-Dichloro-N-methylsulphonyl-aniline | 174 (ethanol) |
| 3,4-Dichloro-N-(4-methyl-benzenesulphonyl)-aniline | 150 (isopropanol) |
| 4-Acetylamino-N-(4-methyl-benzenesulphonyl)-aniline | 184 (petroleum ether 40/80) |
| 3,4-Dichloro-N-(4-methoxy-benzenesulphonyl)-aniline | 90 (isopropanol) |
| 4-Acetylamino-N-methylsulphonyl-aniline | 208 (methanol) |
| N-Methylsulphonyl-4-amino-phenylacetamide | 206 (methanol) |
| N-(4-methyl-benzenesulphonyl)-4-amino-phenylacetamide | 162 (isopropanol) |

(b) 2-Allyloxy-N-[(2,3-epoxy)-propyl]-N-methylsulphonyl-aniline

In a 500 ml three-necked flask, fitted with a mechanical stirrer, a dropping-funnel and a calcium chloride trap, was introduced a suspension of 5.1 g of sodium hydride in 120 ml of dimethylformamide.

While the reaction medium was maintained at or below room temperature, a solution of 55 g. (0.24 mol) of 2-allyloxy-N-methylsulphonyl-aniline was added drop-by-drop and 40 ml of epichlorhydrine were added in one operation. Stirring was continued for three days at room temperature and the reaction medium was poured into water and extracted three times with ether. The organic phase was washed with water and dried on anhydrous calcium sulphate.

The ether was evaporated off and the solid residue was recrystallized from methanol to give 36.5 g of 2-allyloxy-N-[(2,3-epoxy)-propyl]-N-methylsulphonyl-aniline.

Yield: 66.4%. Melting Point: 78° C.

By following the same procedure but using the appropriate starting-products, the compounds listed hereunder were prepared:

| Compounds | Melting Point °C. |
|---|---|
| 2-Allyloxy-N-[(2,3-epoxy)-propyl]-N-(4-methyl-benzenesulphonyl)-aniline | not analysed |
| 2-Allyloxy-N-[(2,3-epoxy)-propyl]-N-(4-methoxy-benzenesulphonyl)-aniline | not analysed |
| 2,6-Dichloro-N-[(2,3-epoxy)-propyl]-N-benzenesulphonyl-aniline | 126–127 (isopropanol) |
| 2,6-Dichloro-N-[(2,3-epoxy)-propyl]-N-(4-methyl-benzenesulphonyl)-aniline | 126 (isopropanol) |
| 3,4-Dichloro-N-[(2,3-epoxy)-propyl]-N-methylsulphonyl-aniline | 75 (isopropanol/chloroforme) |
| 3,4-Dichloro-N-[(2,3-epoxy)-propyl]-N-(4-methyl-benzenesulphonyl)-aniline | 200 (isopropanol/chloroforme) |
| 3,4-Dichloro-N-[(2,3-epoxy)-propyl]-N-(4-methoxy-benzenesulphonyl)-aniline | 110 (isopropanol) |
| 4-Acetylamino-N-[(2,3-epoxy)-propyl]-N-methylsulphonyl-aniline | 136–140 (isopropanol) |
| 4-Acetylamino-N-[(2,3-epoxy)-propyl]-N-(4-methyl-benzenesulphonyl)-aniline | 114–115 (isopropanol) |
| N-[(2,3-epoxy)-propyl]-N-methylsulphonyl-4-amino-phenylacetamide | 154–159 (methanol) |
| N-[(2,3-epoxy)-propyl]-N-(4-methyl-benzenesulphonyl)-4-amino-phenylacetamide | 137–140 (isopropanol) |

(c) 2-Allyloxy-N-(2-hydroxy-3-isopropylamino-propyl)-N-methylsulphonylaniline—Hydrochloride In a one-liter flask were dissolved 56.7 g (0.2 mol) of 2-allyloxy-N-[(2,3-epoxy)-propyl]-N-methylsulphonyl-aniline and 50 ml of isopropylamine in 300 ml of absolute ethanol. The reaction medium was refluxed for 24 hours and the excess of isopropylamine and the solvent was eliminated by evaporation under reduced pressure.

The residue was dissolved in ether and a saturated solution of hydrochloric acid in ether was added.

The hydrochloride precipitated and was filtered and recrystallized from isopropanol to give 58.5 g of 2-allyloxy-N-(2-hydroxy-3-isopropylaminopropyl)-N-methylsulphonyl-aniline.

Yield: 77.4%. Melting Point: 139°–141° C.

By following the same procedure but using the appropriate starting products, the compounds listed hereunder were prepared:

| Compounds | Melting Point °C. |
|---|---|
| 2-Allyloxy-N-(3-terbutylamino-2-hydroxy-propyl)-N-methylsulphonyl-aniline. Hydrochloride | 183 (isopropanol) |
| 2-Allyloxy-N-methylsulphonyl-N-[(2-phenoxyethyl)-3-amino-2-hydroxy-propyl]-aniline. p-toluenesulphonate. | 118–120 (isopropanol) |
| 2-Allyloxy-N-methylsulphonyl-N-(2-hydroxy-3- | 119–121 |

| Compounds | Melting Point °C. |
|---|---|
| pyrrolidino-propyl)-aniline. Acid oxalate | (ethyl acetate/methanol) |
| 2-Allyloxy-N-methysulphonyl-N-[2-hydroxy-(3-phenyl-propyl)-3-amino-propyl]-aniline. Acid oxalate | 154–156 (ethyl acetate/methanol) |
| 2-Allyloxy-N-methylsulphonyl-N-(2-hydroxy-3-morpholino-propyl)-aniline. Acid oxalate | 146–151 (isopropanol) |
| 2-Allyloxy-N-methylsulphonyl-N-[2-hydroxy-3-(4-methyl-piperazinyl)-propyl]-aniline. Dihydrochloride | 223–229 (isopropanol) |
| 2-Allyloxy-N-methylsulphonyl-N-[3-(4-ethyl-1-piperazinyl)-2-hydroxy-propyl]-aniline. Dihydrochloride | 211–213 (acetone) |
| 2-Allyloxy-N-methylsulphonyl-N-[2-hydroxy-3-(4-propyl-1-piperazinyl)-propyl]-aniline. Dihydrochloride | 186–189 (acetone) |
| 2-Allyloxy-N-methylsulphonyl-N-[2-hydroxy-3-(4-phenyl-1-piperazinyl)-propyl]-aniline. Dihydrochloride | 127–131 (acetone) |
| 2-Allyloxy-N-[3-(4-(4-fluoro-phenyl)-1-piperazinyl)-2-hydroxy-propyl]-N-methylsulphonyl-aniline. Acid oxalate | 174–180 (acetone) |
| 2-Allyloxy-N-[3-(4-(2-hydroxy-ethyl)-1-piperazinyl)-2-hydroxy-propyl]-N-methylsulphonyl-aniline | 148–151 (isopropanol) |
| 2-Allyloxy-N-[2-hydroxy-3-(4-(2-pyridyl)-1-piperazinyl)-propyl]-N-methylsulphonyl-aniline. Neutral oxalate | 175–181 (methanol) |
| 2-Allyloxy-N-[3-(4-(3-chloro-phenyl)-1-piperazinyl)-2-hydroxy-propyl]-N-methylsulphonyl-aniline. Acid oxalate | 150–155 (acetone) |
| 2-Allyloxy-N-[3-(4-(4-chloro-phenyl)-1-piperazinyl)-2-hydroxy-propyl]-N-methylsulphonyl-aniline. Acid oxalate | 163–166 (acetone) |
| 2-Allyloxy-N-[2-hydroxy-3-(4-(4-methoxy-phenyl)-1-piperazinyl)-propyl]-N-methylsulphonyl-aniline. Acid oxalate | 116–118 (acetone) |
| 2-Allyloxy-N-[3-(4-benzyl-1-piperazinyl)-2-hydroxy-propyl]-N-methylsulphonyl-aniline. Difumarate | 175–177.5 (isopropanol) |
| 2-Allyloxy-N-[2-hydroxy-3-(4-(2-methoxy-phenyl)-1-piperazinyl)-propyl]-N-methylsulphonyl-aniline. Hydrochloride | 170–173 (isopropanol) |
| 2-Allyloxy-N-[3-(4-(2-fluoro-phenyl)-1-piperazinyl)-2-hydroxy-propyl]-N-methylsulphonyl-aniline | 159–165 (isopropanol) |
| 2-Allyloxy-N-(2-hydroxy-3-isopropylamino-propyl)-N-(4-methyl-benzenesulphonyl)-aniline Hydrochloride | 165–166 (isopropanol) |
| 2-Allyloxy-N-(3-tert-butylamino-2-hydroxy-propyl)-N-(4-methyl-benzenesulphonyl)-aniline. Hydrochloride | 126 (ethyl acetate) |
| 2-Allyloxy-N-(2-hydroxy-3-pyrrolidino-propyl)-N-(4-methyl-benzenesulphonyl)-aniline. Hydrochloride | 144–146.5 (isopropanol) |
| 2-Allyloxy-N-(2-hydroxy-3-morpholino-propyl)-N-(4-methyl-benzenesulphonyl)-aniline. Hydrochloride | 81–84 (isopropanol) |
| 2-Allyloxy-N-[2-hydroxy-3-(2-phenoxy-ethylamino)-propyl]-N-(4-methyl-benzenesulphonyl)-aniline. Hydrochloride | 143–145 (isopropanol) |
| 2-Allyloxy-N-[2-hydroxy-3-(3-phenyl-propylamino)-propyl]-N-(4-methyl-benzenesulphonyl)-aniline. Neutral oxalate | 167–168 (ethanol) |
| 2-Allyloxy-N-[2-hydroxy-3-(4-methyl-1-piperazinyl)-propyl]-N-(4-methyl-benzenesulphonyl)-aniline. Dihydrochloride | 176–185 |
| 2-Allyloxy-N-[3-(4-(4-ethyl-1-piperazinyl)-2-hydroxy-propyl]-N-(4-methyl-benzenesulphonyl)-aniline. Dihydrochloride | (isopropanol) 159–164 (isopropanol) |
| 2-Allyloxy-N-[2-hydroxy-3-(4-propyl-1-piperazinyl)-propyl]-N-(4-methyl-benzenesulphonyl)-aniline | 144–148 (isopropanol) |
| 2-Allyloxy-N-[2-hydroxy-3-(4-(2-hydroxy-ethyl)-1-piperazinyl)-propyl]-N-(4-methyl-benzenesulphonyl)-aniline. Dihydrochloride | 157–159 (isopropanol) |
| 2-Allyloxy-N-[3-(4-(4-chloro-phenyl)-1-piperazinyl)-2-hydroxy-propyl]-N-(4-methyl-benzenesulphonyl)-aniline. Neutral oxalate | 176–177 (methanol) |
| 2-Allyloxy-N-[2-hydroxy-3-(4-(2-pyridyl)-1-piperazinyl)-propyl]-N-(4-methyl-benzenesulphonyl)-aniline. Neutral oxalate | 203–204.5 (methanol) |
| 2-Allyloxy-N-[2-hydroxy-3-(4-phenyl-1-piperazinyl)-propyl]-N-(4-methyl-benzenesulphonyl)-aniline. Hydrochloride | 193–203 (methanol) |
| 2-Allyloxy-N-[3-(4-(3-chloro-phenyl)-1-piperazinyl)-2-hydroxy-propyl]-N-(4-methyl-benzenesulphonyl)-aniline. Neutral oxalate | 177–179 (acetone) |
| 2-Allyloxy-N-[3-(4-benzyl-1-piperazinyl)-2-hydroxy-propyl]-N-(4-methyl-benzenesulphonyl)-aniline. Dihydrochloride | 142–146 (acetone) |
| 2-Allyloxy-N-[3-(4-(4-fluoro-phenyl)-1-piperazinyl)-2-hydroxy-propyl]-N-(4-methyl-benzenesulphonyl)-aniline. Hydrochloride | 191–194 (isopropanol) |
| 2-Allyloxy-N-[2-hydroxy-3-(4-(4-methoxy-phenyl)-1-piperazinyl)-propyl]-N-(4-methyl-benzenesulphonyl)-aniline. Hydrochloride | 211–214 (methanol) |
| 2-Allyloxy-N-[2-hydroxy-3-(4-(2-methoxy-phenyl)-1-piperazinyl)-propyl]-N-(4-methyl-benzenesulphonyl)-aniline. Neutral oxalate | 161–165 (isopropanol) |
| 2-Allyloxy-N-[3-(4-(2-fluoro-phenyl)-1-piperazinyl)-2-hydroxy-propyl]-N-(4-methyl-benzenesulphonyl)-aniline. Hydrochloride | 160–165 (isopropanol) |
| 2-Allyloxy-N-(2-hydroxy-3-isopropylamino-propyl)-N-(4-methoxy-benzenesulphonyl)-aniline. Hydrochloride | 137–140 (isopropanol) |
| 2-Allyloxy-N-(3-tert-butylamino-2-hydroxy-propyl)-N-(4-methoxy-benzenesulphonyl)-aniline. Hydrochloride | 129–130 (isopropanol) |
| 2-Allyloxy-N-[2-hydroxy-3-(2-phenoxy-ethylamino)-propyl]-N-(4-methoxy-benzenesulphonyl)-aniline. Hydrochloride | 162–164 (ethyl acetate) |
| 2-Allyloxy-N-[2-hydroxy-3-(3-phenyl-propylamino)-propyl]-N-(4-methoxy-benzenesulphonyl)-aniline. Neutral oxalate | 157–158 (ethyl acetate) |
| 2-Allyloxy-N-(2-hydroxy-3-pyrrolidino-propyl)-N-(4-methoxy-benzenesulphonyl)-aniline. Hydrochloride | 161–162.5 (ethyl acetate) |
| 2-Allyloxy-N-(2-hydroxy-3-morpholino-propyl)-N-(4-methoxy-benzenesulphonyl)-aniline. Hydrochloride | 124–127 (isopropanol) |
| 2-Allyloxy-N-[2-hydroxy-3-(4-methyl-1-piperazinyl)-propyl]-N-(4-methoxy-benzenesulphonyl)-aniline. Dihydrochloride | 191–193 (isopropanol) |
| 2-Allyloxy-N-[3-(4-ethyl-1-piperazinyl)-2-hydroxy-propyl]-N-(4-methoxy-benzenesulphonyl)-aniline. Dihydrochloride | 147–150 (isopropanol) |
| 2-Allyloxy-N-[2-hydroxy-3-(4-n-propyl-1-piperazinyl)-propyl]-N-(4-methoxy-benzenesulphonyl)-aniline. Dihydrochloride | 181–184 (acetone) |
| 2-Allyloxy-N-[2-hydroxy-3-(4-(2-hydroxy-ethyl)- | |

| Compounds | Melting Point °C. |
|---|---|
| 1-piperazinyl)-propyl]-N-(4-methoxy-benzene-sulphonyl)-aniline. Dihydrochloride | 195–197 (methanol) |
| 2-Allyloxy-N-[2-hydroxy-3-(4-phenyl-1-piperazinyl)-propyl]-N-(4-methoxy-benzenesulphonyl)-aniline. Hydrochloride | 220–222 (isopropanol) |
| 2-Allyloxy-N-[3-(4-benzyloxy-1-piperazinyl)-2-hydroxy-propyl]-N-(4-methoxy-benzenesulphonyl)-aniline. Dihydrochloride | 144–147 (acetone) |
| 2-Allyloxy-N-[3-(4-(3-chloro-phenyl)-1-piperazinyl)-2-hydroxy-propyl]-N-(4-methoxy-benzenesulphonyl)-aniline. Neutral oxalate | 171–175 (acetone) |
| 2-Allyloxy-N-[2-hydroxy-3-(4-(4-methoxy-phenyl)-1-piperazinyl)-propyl]-N-(4-methoxy-benzenesulphonyl)-aniline. Neutral oxalate | 161–164 (isopropanol) |
| 2-Allyloxy-N-[2-hydroxy-3-(4-(2-pyridyl)-1-piperazinyl)-propyl]-N-(4-methoxy-benzenesulphonyl)-aniline. Neutral oxalate | 183–185 (acetone) |
| 2-Allyloxy-N-[3-(4-(4-chloro-phenyl)-1-piperazinyl)-2-hydroxy-propyl]-N-(4-methoxy-benzenesulphonyl)-aniline. Acid oxalate | 123–124 (acetone) |
| 2-Allyloxy-N-[3-(4-(4-fluoro-phenyl)-1-piperazinyl)-2-hydroxy-propyl]-N-(4-methoxy-benzene-sulphonyl)-aniline. Neutral oxalate | 160–161.5 (methanol) |
| 2-Allyloxy-N-[2-hydroxy-3-(4-(2-methoxy-phenyl)-1-piperazinyl)-propyl]-N-(4-methoxy-benzene-sulphonyl)-aniline | 185–188.5 (isopropanol) |
| 2-Allyloxy-N-[2-hydroxy-3-(4-(2-fluoro-phenyl)-1-piperazinyl)-propyl]-N-(4-methoxy-benzene-sulphonyl)-aniline | 175–179 (isopropanol) |
| 2,6-Dichloro-N-benzenesulphonyl-N-[2-hydroxy-3-(4-methyl-1-piperazinyl)-propyl]-aniline. Dihydrochloride | 239–243 (acetone) |
| 2,6-Dichloro-N-benzenesulphonyl-N-[2-hydroxy-3-(4-phenyl-1-piperazinyl)-propyl]-aniline | 131–134 (isopropanol) |
| 2,6-Dichloro-N-benzenesulphonyl-N-[2-hydroxy-3-(4-(4-chloro-phenyl)-1-piperazinyl)-propyl]-aniline. Acid oxalate | 137–143 (acetone) |
| 2,6-Dichloro-N-benzenesulphonyl-N-[3-(4-benzyl-1-piperazinyl)-2-hydroxy-propyl]-aniline. Dihydrochloride | 220–228 (acetone) |
| 2,6-Dichloro-N-benzenesulphonyl-N-[2-hydroxy-3-(4-(4-methoxy-phenyl)-1-piperazinyl)-propyl]-aniline. Acid oxalate | 131–136 (acetone) |
| 2,6-Dichloro-N-benzenesulphonyl-N-[3-(4-(3-chloro-phenyl)-1-piperazinyl)-2-hydroxy-propyl]-aniline. Acid oxalate | 188–189 (methanol) |
| 2,6-Dichloro-N-benzenesulphonyl-N-[2-hydroxy-3-(4-fluoro-4-phenyl-1-piperazinyl)-propyl]-aniline. Acid oxalate | 174–176 (isopropanol) |
| 2,6-Dichloro-N-benzenesulphonyl-N-[2-hydroxy-3-(4-(2-methoxy-phenyl)-1-piperazinyl)-propyl]-aniline. Acid oxalate | 196–197 (isopropanol) |
| 2,6-Dichloro-N-[2-hydroxy-3-(4-phenyl-1-piperazinyl-propyl]-N-(4-methyl-benzenesulphonyl)-aniline. Dihydrochloride | 230–234 (acetone) |
| 2,6-Dichloro-N-[2-hydroxy-3-(4-(4-methoxy-phenyl)-1-piperazinyl)-propyl]-N-(4-methyl-benzenesulphonyl)-aniline. Neutral oxalate | 164–169 (acetone) |
| 2,6-Dichloro-N-[2-hydroxy-3-(4-phenyl-1-piperazinyl)-propyl]-N-(4-methyl-benzenesulphonyl)-aniline. Acid oxalate | 230–234 (acetone) |
| 2,6-Dichloro-N-[3-(4-(4-benzyl-phenyl)-1-piperazinyl)-2-hydroxy-propyl]-N-(4-methyl-benzenesulphonyl)-aniline. Dihydrochloride | 185–187 (acetone) |
| 2,6-Dichloro-N-[3-(4-(4-chloro-phenyl)-1-piperazinyl)-2-hydroxy-propyl]-N-(4-methyl-benzenesulphonyl)-aniline. Acid oxalate | 152–155 (acetone) |
| 2,6-Dichloro-N-[3-(4-(3-chloro-phenyl)-1-piperazinyl)-2-hydroxy-propyl]-N-(4-methyl-benzene-sulphonyl)-aniline. Acid oxalate | 167–169 (acetone) |
| 2,6-Dichloro-N-[3-(4-(4-fluoro-phenyl)-1-piperazinyl)-2-hydroxy-propyl]-N-(4-methyl-benzenesulphonyl)-aniline. Acid oxalate | 167–169 (acetone) |
| 2,6-Dichloro-N-[2-hydroxy-3-(4-(2-methoxy-phenyl)-1-piperazinyl)-propyl]-N-(4-methyl-benzenesulphonyl)-aniline. Acid oxalate | 192–195 (acetone) |
| 3,4-Dichloro-N-[2-hydroxy-3-(4-methyl-1-piperazinyl)-propyl]-N-methylsulphonyl-aniline. Dihydrochloride | 224 (ethanol) |
| 3,4-Dichloro-N-[3-(4-(2-chloro-phenyl)-1-piperazinyl)-2-hydroxy-propyl]-N-methylsulphonyl-aniline. Hydrochloride | 115–117 (ethanol) |
| 3,4-Dichloro-N-[3-(4-(2-chloro-phenyl)-1-piperazinyl)-2-hydroxy-propyl]-N-methylsulphonyl-aniline. Dihydrochloride | 186 (ethanol) |
| 3,4-Dichloro-N-[2-hydroxy-3-(4-(2-methoxy-phenyl)-1-piperazinyl)-propyl]-N-methylsulphonyl-aniline. Dihydrochloride | 209–210 (isopropanol) |
| 3,4-Dichloro-N-[2-hydroxy-3-(4-(4-methoxy-phenyl)-1-piperazinyl)-propyl]-N-methylsulphonyl-aniline. Dihydrochloride | 195 (ethanol) |
| 3,4-Dichloro-N-[2-hydroxy-3-(4-phenyl-1-piperazinyl)-propyl]-N-methylsulphonyl-aniline. | 107–108 (ethanol) |
| 3,4-Dichloro-N-[2-hydroxy-3-(4-methyl-1-piperazinyl)-propyl]-N-(4-methyl-benzenesulphonyl)-aniline. Dihydrochloride | 250 (isopropanol) |
| 3,4-Dichloro-N-[2-hydroxy-3(4-phenyl-1-piperazinyl)-propyl]-N-(4-methyl-benzenesulphonyl)-aniline | 163–164 (isopropanol) |
| 3,4-Dichloro-N-[2-hydroxy-3-(4-methyl-1-piperazinyl)-propyl]-N-(4-methoxy-benzenesulphonyl)-aniline. Dihydrochloride | 237–238 (isopropanol) |
| 3,4-Dichloro-N-[2-hydroxy-3-(4-methyl-1-piperazinyl)-propyl]-N-(4-methoxy-benzenesulphonyl)-aniline | 152–153 (ethanol) |
| 3,4-Dichloro-N-[3-(4-(4-chloro-phenyl)-1-piperazinyl)-2-hydroxy-propyl]-N-(4-methoxy-benzene sulphonyl)-aniline. Dihydrochloride | 164–165 (isopropanol) |
| 3,4-Dichloro-N-[2-hydroxy-3-(4-(4-methoxy-phenyl)-1-piperazinyl)-propyl]-N-(4-methoxy-benzene-sulphonyl)-aniline. Dihydrochloride | 181–182 (ethanol) |
| 4-Acetylamino-N-[2-hydroxy-3-(4-methyl-1-piperazinyl)-propyl]-N-methylsulphonyl-aniline. Dihydrochloride | 205–208 (methanol) |
| 4-Acetylamino-N-[3-(4-(4-chloro-phenyl)-1-piperazinyl)-2-hydroxy-propyl]-N-methylsulphonyl-aniline | 167–168 (ethanol) |
| 4-Acetylamino-N-[2-hydroxy-3-(4-phenyl-1-piperazinyl)-propyl]-N-methylsulphonyl-aniline | 177–179 (methanol) |
| 4-Acetylamino-N-[2-hydroxy-3-(4-(4-methoxy-phenyl)-1-piperazinyl)-propyl]-N-methylsulphonyl-aniline | 195–197 (ethanol) |
| 4-Acetylamino-N-[2-hydroxy-3-(4-(2-methoxy-phenyl)-1-piperazinyl)-propyl]-N-methylsulphonyl-aniline | 130–133 (ethanol) |
| 4-Acetylamino-N-[3-(4-(2-chloro-phenyl)-1-piperazinyl)-2-hydroxy-propyl]-N-methylsulphonyl-aniline | 142–144 (isopropanol) |
| 4-Acetylamino-N-[2-hydroxy-3-(4-phenyl-1-piperazinyl)-propyl]-N-(4-methyl-benzenesulphonyl)-aniline | 175–177 (ethanol) |
| 4-Acetylamino-N-[2-hydroxy-3-(4-(4-methoxy-phenyl)-1-piperazinyl)-propyl]-N-(4-methyl-benzene-(sulphonyl)-aniline. Dihydrochloride | 158–162 (methanol) |
| 4-Acetylamino-N-[2-hydroxy-3-(4-(2-methoxy-phenyl)-1-piperazinyl)-propyl]-N-(methyl-benzene-sulphonyl)-aniline. Hydrochloride | 137–142 (ethanol) |
| 4-Acetylamino-N-[3-(4-(2-chloro-phenyl)-1-piperazinyl)-2-hydroxy-propyl]-N-(4-methyl-benzene-sulphonyl)-aniline. Hydrochloride | 170–172 (ethanol) |
| 4-Acetylamino-N-[3-(4-(4-chloro-phenyl)-1-piperazinyl)-2-hydroxy-propyl]-N-(4-methyl-benzenesulphonyl)-aniline | 177–178 (ethanol) |
| N-[2-hydroxy-3-(4-methyl-1-piperazinyl)-propyl]-N-methylsulphonyl-4-amino-phenylacetamide | 129–135 (isopropanol/ether) |
| N-[2-hydroxy-3-(4-phenyl-1-piperazinyl)-propyl]-N-methylsulphonyl-4-amino-phenylacetamide | 155–157 (ethanol) |
| N-[3-(4-(4-chloro-phenyl)-1-piperazinyl)-2-hydroxy-propyl]-N-methylsulphonyl-4-amino-phenylacetamide | 172–173 (ethanol) |

-continued

| Compounds | Melting Point °C. |
|---|---|
| N-[3-(4-(2-chloro-phenyl)-1-piperazinyl)-2-hydroxy-propyl]-N-methylsulphonyl-4-amino-phenyl-acetamide | 177–178 (ethanol) |
| N-[2-hydroxy-3-(4-(4-methoxy-phenyl)-1-piperazinyl)-propyl]-N-methylsulphonyl-4-amino-phenyl-acetamide | 171–172 (ethanol) |
| N-[2-hydroxy-3-(4-(2-methoxy-phenyl)-1-piperazinyl)-propyl]-N-methylsulphonyl-4-amino-phenyl-acetamide | 195–197 (ethanol) |
| N-[2-hydroxy-3-(4-methyl-1-piperazinyl)-propyl]-N(4-methyl-benzenesulphonyl-4-amino-phenyl-acetamide. Dihydrochloride | 217–219 (ethanol) |
| N-[2-hydroxy-3-(4-phenyl-1-piperazinyl)-propyl]-N-(4-methyl-benzenesulphonyl)-4-amino-phenylacetamide | 158–161 (ethanol) |
| N-[2-hydroxy-3-(4-(2-methoxy-phenyl)-1-piperazinyl)-propyl]-N-(4-methyl-benzenesulphonyl)-4-amino-phenylacetamide | 145–147 (ethanol) |
| N-[3-(4-(4-chloro-phenyl)-1-piperazinyl)-2-hydroxy-propyl]-N-(4-methyl-benzenesulphonyl)-4-amino-phenylacetamide | 177–179 (ethanol) |
| N-[3-(4-(2-chloro-phenyl)-1-piperazinyl)-2-hydroxy-propyl]-N-(4-methyl-benzenesulphonyl)-4-amino-phenylacetamide | 160–161 (ethanol) |
| N-[2-hydroxy-3-(4-(4-methoxy-phenyl)-1-piperazinyl)-propyl]-N-(4-methyl-benzenesulphonyl)-4-amino-phenylacetamide | 157–158 (ethanol) |

Pharmaceutical compositions were prepared in accordance with known pharmaceutical techniques:

| Ingredients | mg |
|---|---|
| (1) Hard gelatin capsule | |
| 2-Allyloxy-N-(3-tert-butylamino-2-hydroxy-propyl)-N-(4-methoxy-benzenesulphonyl)-aniline. Hydrochloride | 100 |
| Starches | 99.5 |
| Colloidal silicia | 0.5 |
| | 200.0 |
| (2) Injectable solution | |
| 2-Allyloxy-N-[3-(4-benzyl-1-piperazinyl)-2-hydroxy-propyl]-N-(4-methyl-benzenesulphonyl)-aniline. Dihydrochloride | 150 |
| Polysorbate 80 | 150 |
| Benzyl alcohol | 75 |
| Water to 3 ml | |
| (3) Suppository | |
| 2-Allyloxy-N-[2-hydroxy-3-(4-(2-methoxy-phenyl)-1-piperazinyl)-propyl]-N-methylsulphonyl-aniline. Hydrochloride | 100 |
| Mixture of saturated acid mono- and diglycerides ($C_{12}$–$C_{18}$) | 1400 |
| | 1500 |
| (4) Tablet | |
| 4-Acetylamino-N-[2-hydroxy-3-(4-phenyl-1-piperazinyl)-propyl]-N-methylsulphonyl-aniline | 200 |
| Lactose | 64 |
| Polyvinylpyrrolidone | 6 |
| Sodium carboxymethyl starch | 24 |
| Magnesium stearate | 4 |
| Talc | 2 |
| | 300 |

We claim:
1. Compounds of the formula:

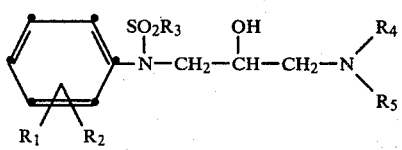

and the pharmaceutically acceptable acid addition salts thereof, wherein $R_1$ and $R_2$, which are the same or different, represent an allyloxy, acetamide or carboxamide group or a hydrogen or chlorine atom, $R_3$ represents a methyl, phenyl, methylphenyl or methoxyphenyl group, $R_4$ represents a hydrogen atom and $R_5$ an isopropyl, terbutyl, 2-phenoxy-ethyl, 3-phenyl-propyl group, or $R_4$ and $R_5$ taken together form with the nitrogen atom a heterocycle such as pyrrole, morpholine or a substituted piperazine of the formula:

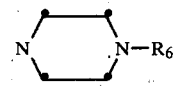

wherein $R_6$ represents a straight-chain alkyl group containing from 1 to 3 carbon atoms, a 2-hydroxyethyl, a benzyl or a 2-pyridyl group or a phenyl group optionally substituted by either a halogen atom or by a methoxy radical.

2. 2-Allyloxy-N-(3-tert-butylamino-2-hydroxy-propyl)-N-(4-methoxybenzenesulphonyl)-aniline.

3. 2-Allyloxy-N-[2-hydroxy-3-(4-(2-methoxy-phenyl)-1-piperazinyl)-propyl]-N-methylsulphonyl-aniline.

4. 2-Allyloxy-N-[3-(4-benzyl-1-piperazinyl)-2-hydroxy-propyl]-N-(4-methyl-benzenesulphonyl)-aniline.

5. 4-Acetylamino-N-[2-hydroxy-3-(4-phenyl-1-piperazinyl)-propyl]-N-methylsulphonyl-aniline.

6. The compound of claim 1 wherein $R_1$ is hydrogen, $R_2$ is allyloxy, $R_3$ is methyl, $R_4$ and $R_5$ taken together form with the nitrogen atom a piperazine radical wherein $R_6$ is 4-fluorophenyl.

7. The compound of claim 1 wherein $R_1$ is hydrogen, $R_2$ is allyloxy, $R_3$ is 4-methoxyphenyl, $R_4$ and $R_5$ taken together form with the nitrogen atom a piperazine radical wherein $R_6$ is 2-pyridyl.

8. The compound of claim 1 wherein $R_1$ is hydrogen, $R_2$ is allyloxy, $R_3$ is 4-methoxyphenyl, $R_4$ and $R_5$ taken together form with the nitrogen atom a piperazine radical wherein $R_6$ is 2-fluorophenyl.

9. The compound of claim 1 wherein $R_1$ and $R_2$ are chlorine, $R_3$ is methyl, $R_4$ and $R_5$ taken together form with the nitrogen atom a piperazine radical wherein $R_6$ is 2-chlorophenyl.

10. The compound of claim 1 wherein $R_1$ is hydrogen, $R_2$ is allyloxy, $R_3$ is 4-methoxyphenyl, $R_4$ and $R_5$ taken together form with the nitrogen atom a piperazine radical wherein $R_6$ is 2-methoxyphenyl.

11. The compound of claim 1 wherein $R_1$ and $R_2$ are chlorine, $R_3$ is 4-methoxyphenyl, $R_4$ and $R_5$ taken together form with the nitrogen atom a piperazine radical wherein $R_6$ is 4-chlorophenyl.

12. The compound of claim 1 wherein $R_1$ is hydrogen, $R_2$ is 4-acetylamino, $R_3$ is methyl, $R_4$ and $R_5$ taken together form with the nitrogen atom a piperazine radical wherein $R_6$ is 4-chlorophenyl.

13. The compound of claim 1 wherein $R_1$ is hydrogen, $R_2$ is 4-acetylamino, $R_3$ is 4-methylphenyl, $R_4$ and $R_5$ taken together form with the nitrogen atom a piperazine radical wherein $R_6$ is phenyl.

14. The compound of claim 1 wherein $R_1$ is hydrogen, $R_2$ is 4-acetylamino, $R_3$ is 4-methylphenyl, $R_4$ and $R_5$ taken together form with the nitrogen atom a piperazine radical wherein $R_6$ is 2-methoxyphenyl.

15. The compound of claim 1 wherein $R_1$ is hydrogen, $R_2$ is 4-acetylamino, $R_3$ is 4-methylphenyl, $R_4$ and $R_5$ taken together form with the nitrogen atom a piperazine radical wherein $R_6$ is 2-chlorophenyl.

16. The compound of claim 1 wherein $R_1$ and $R_2$ are hydrogen, $R_3$ is methyl, $R_4$ and $R_5$ taken together form with the nitrogen atom a piperazine radical wherein $R_6$ is 4-chlorophenyl.

17. The compound of claim 1 wherein $R_1$ is hydrogen, $R_2$ is $NH_2COCH_2-$, $R_3$ is methyl, $R_4$ and $R_5$ taken together with the nitrogen atom form a piperazine radical wherein $R_6$ is 2-methoxyphenyl.

18. The compound of claim 1 wherein $R_1$ is hydrogen, $R_2$ is $NH_2COCH_2-$, $R_3$ is 4-methylphenyl, $R_4$ and $R_5$ taken together with the nitrogen atom form a piperazine radical wherein $R_6$ is 2-methoxyphenyl.

19. Method of treatment of angina pectoris whereby from 100 to 200 mg per day of at least one compound of formula I of claim 1 or a pharmaceutically acceptable acid addition salt thereof are administered to the said patient.

20. Pharmaceutical composition for the treatment of angina pectoris containing as active ingredient at least one compound of formula I of claim 1, or a pharmaceutically acceptable acid addition salt thereof, together with an appropriate excipient or carrier therefor, the active ingredient being present in the amount of 100 milligrams to 200 milligrams per dosage unit form.

21. Pharmaceutical composition according to claim 20 for oral or rectal administration.

22. Pharmaceutical composition according to claim 20 in the form of an injectable solution.

* * * * *